United States Patent
Chen et al.

(10) Patent No.: US 8,329,651 B2
(45) Date of Patent: Dec. 11, 2012

(54) METHOD FOR RENAL DISEASE DIAGNOSIS AND PROGNOSIS USING ANNEXIN A1 AND RAB23 AS MARKERS

(75) Inventors: Ann Chen, Taipei (TW); Hao-Ai Shui, Taipei (TW); Shuk-Man Ka, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 12/486,166

(22) Filed: Jun. 17, 2009

(65) Prior Publication Data

US 2010/0203512 A1    Aug. 12, 2010

(30) Foreign Application Priority Data

Feb. 10, 2009    (TW) .............................. 98104215 A

(51) Int. Cl.
  *A61P 13/12* (2006.01)
  *G01N 33/48* (2006.01)
(52) U.S. Cl. .................... 514/15.4; 435/287.2
(58) Field of Classification Search .................... None
  See application file for complete search history.

(56) References Cited

U.S. PATENT DOCUMENTS

| | | | |
|---|---|---|---|
| 6,410,708 B1 * | 6/2002 | Ashkenazi et al. | 536/23.5 |
| 6,653,445 B1 * | 11/2003 | Ni et al. | 530/350 |
| 6,905,827 B2 | 6/2005 | Wohlgemuth et al. | |
| 7,026,121 B1 | 4/2006 | Wohlgemuth et al. | |
| 7,235,358 B2 | 6/2007 | Wohlgemuth et al. | |
| 2002/0168711 A1 | 11/2002 | Rosen et al. | |
| 2004/0009479 A1 | 1/2004 | Wohlgemuth et al. | |
| 2004/0072160 A1 | 4/2004 | Mendrick et al. | |
| 2005/0191312 A1 | 9/2005 | Raitano et al. | |
| 2005/0208544 A1 | 9/2005 | Broeckhoven et al. | |
| 2005/0239146 A1 | 10/2005 | Tainsky et al. | |
| 2006/0024315 A1 * | 2/2006 | Schnitzer et al. | 424/155.1 |
| 2006/0078900 A1 | 4/2006 | Mendrick et al. | |
| 2007/0093969 A1 | 4/2007 | Mendrick et al. | |
| 2007/0124086 A1 | 5/2007 | Mendrick et al. | |
| 2007/0134261 A1 | 6/2007 | Hancock et al. | |
| 2007/0154897 A1 | 7/2007 | Yen et al. | |
| 2007/0161022 A1 | 7/2007 | Kim et al. | |

FOREIGN PATENT DOCUMENTS

EP    1724585    * 11/2006

OTHER PUBLICATIONS

Oh et al., Subtractive proteomic mapping of the endothelial surface in lung and solid tumors for tissue-specific therapy Nature, 429, 629-635, 2004.*
Lim et al., Annexin 1: the new face of an old molecule, FASEB J., 21, 968-975, 2007.*
Alves et al., "Annexin A1 Subcellular Expression in Laryngeal Squamous Cell Carcinoma." *Histopathology*, vol. 53, pp. 715-727 (2008).
Hou et al., "Integrative Genomics Identifies *RAB23* as an Invasion Mediator Gene in Diffuse-Type Gastric Cancer." *Cancer Research*, vol. 68, No. 12, pp. 4623-4630 (2008).
Huang et al., "Rab 23 is Expressed in the Glomerulus and Pays a Role in the Development of Focal Segmental Glomerulosclerosis." *Nephrol Dial Transplant*, vol. 24, pp. 743-754 (2008).
Ishido., "Overexpression of Bcl-2 Inhibits Nuclear Localization of Annexin I During Tumor Necrosis Factor-Alpha-Mediated Apoptosis in Porcine Renal LLC-PK1 Cells." *Reulatory Peptides*, vol. 124, pp. 45-51 (2005).
Kim et al., "PKCδ-Dependent Cleavage and Nuclear Translocation of Annexin A1 by Phorbol 12-Myrisate 12-Acetate." *Eur. J. Biochem.*, vol. 270, pp. 4089-4094 (2003).
Patterson et al., "Mouse *Hitchhiker* Mutants have Spina Bifida, Dorso-Ventral Patterning Defects and Polydactyly: Identification of Tulp3 as a Novel Negative Regulator of the Sonic Hedgehog Pathway." *Human Molecular Genetics*, vol. 18, No. 10, pp. 1719-1739 (2009).
Perretti et al., "Annexin A1 and Glucocorticoids as Effectors of the Resolution of Inflammation." Perspectives, www.nature.com/reviews/immunol, vol. 9, pp. 62-70 (2009).
Tagoe et al., "Annexin-1 Mediates TNF-α-Stimulated Matrix Metalloproteinase Secretion From Rheumatoid Arthritis Synovial Fibroblasts." *The Journal of Immunology* pp. 2813-2820 (2008).

* cited by examiner

*Primary Examiner* — Elly-Gerald Stoica
(74) *Attorney, Agent, or Firm* — Rosenberg, Klein & Lee

(57) ABSTRACT

Use of Annexin A1 or Rab23 as a biomarker for diagnosing kidney disease or assessing efficacy of kidney disease treatment.

8 Claims, 5 Drawing Sheets

A.

B.

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence

```
<220> FEATURE:
<223> OTHER INFORMATION: PCR Primer

<400> SEQUENCE: 1
ttgaggaggt tgttttagct ctg                                         23

<210> SEQ ID NO 2
<211> LENGTH: 23
<212> TYPE: DNA
<213> ORGANISM: Artificial Sequence
<220> FEATURE:
<223> OTHER INFORMATION: PCR Primer

<400> SEQUENCE: 2
agttcttgat gccaaaatct caa                                         23

<210> SEQ ID NO 3
<211> LENGTH: 24
<212> TYPE: DNA
<213> ORGANISM: Artificial Sequence
<220> FEATURE:
<223> OTHER INFORMATION: PCR Primer

<400> SEQUENCE: 3
gaaggaggac ctcaacgtga gtga                                        24

<210> SEQ ID NO 4
<211> LENGTH: 23
<212> TYPE: DNA
<213> ORGANISM: Artificial Sequence
<220> FEATURE:
<223> OTHER INFORMATION: PCR Primer

<400> SEQUENCE: 4
ccaagtgact tctgaccgat gca                                         23
```

METHOD FOR RENAL DISEASE DIAGNOSIS AND PROGNOSIS USING ANNEXIN A1 AND RAB23 AS MARKERS

CROSS-REFERENCE TO RELATED APPLICATION

This application claims priority to Taiwanese Patent Application 098104215, filed Feb. 10, 2009, the content of which is hereby incorporated by reference in its entirety.

BACKGROUND OF THE INVENTION

Renal disease affects millions of people each year. Early diagnosis greatly improves efficacy of renal disease treatment. Thus, there is a need for developing an accurate method for diagnosing renal disease.

SUMMARY OF THE INVENTION

The present invention is based on the unexpected discoveries that Annexin A1 and Rab23 levels are elevated in kidney specimens and urine samples of patients suffering from various kidney disorders as compared to healthy humans.

Accordingly, one aspect of the present invention features a method of diagnosing a renal disorder in a subject (e.g., a human) using either Annexin A1 or Rab23 as a marker. This method includes (i) providing a renal sample (e.g., a kidney tissue sample or a urine sample) obtained from a subject, (ii) detecting the level of Annexin A1 or Rab23 in the renal sample, and (iii) determining whether the subject suffers from or is at risk for a renal disorder (e.g., kidney sclerosis, kidney fibrosis, glomerular injury, kidney failure, glomerulosclerosis, or glomerulonephritis) based on the Annexin A1 or Rab23 level thus detected. An elevated level in the subject relative to that in a healthy subject indicates that the subject has or is at risk for the renal disorder. The level of Annexin A1 or Rab23 can be determined by examining either its protein or message RNA level. When Rab23 is used as a marker, its level can also be determined by the amount of Shh, Ihh, Dhh, PTCH1, PTCH2, SMO, Gli1, Gli2, Gli3, or a combination thereof.

Another aspect of this invention features a method of assessing the efficacy of a renal disease treatment in a patient. This method includes (i) detecting the level of either Annexin A1 or Rab23 in the kidney of a patient before and after the treatment, and (ii) determining efficacy of the treatment based on a change of the Annexin A1 or Rab23 level after the treatment. A decreased level of either indicates that the treatment is effective in that patient.

Also within the scope of this invention is use of Annexin A1 or Rab23 as a biomarker for diagnosing a kidney disease and assessing efficacy of a kidney disease treatment, and for manufacturing kits used for the just-mentioned purposes.

The details of one or more embodiments of the invention are set forth in the description below. Other features or advantages of the present invention will be apparent from the following drawings and detailed description of several examples, and also from the appended claims.

BRIEF DESCRIPTION OF THE DRAWINGS

The drawings are first described.

DETAILED DESCRIPTION OF THE INVENTION

Figure 1:
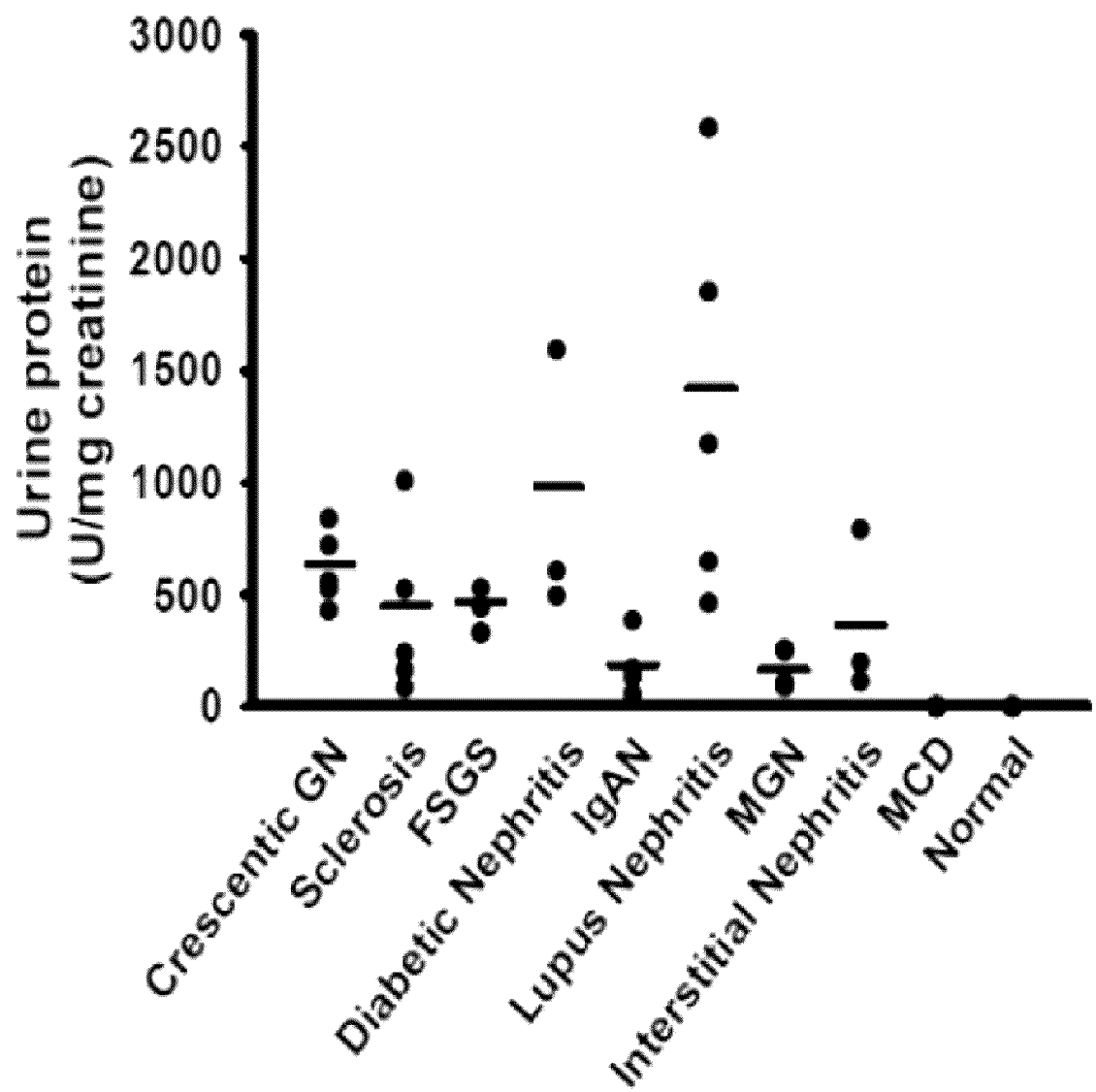
FIG. 1 is a chart showing the protein levels of Annexin A1 in urine samples obtained from patents having various kidney diseases.

We have discovered that the expression levels of Annexin A1 and Rab23 are elevated in patients suffering from various kidney diseases as compared to those in healthy humans. We have also discovered that the level of Annexin A1 or Rab23 correlates with disease severity. Accordingly, disclosed herein is a method of using Annexin A1 or Rab23 as a biomarker for diagnosing a kidney disease or for assessing the efficacy of a kidney disease treatment in a patient. See Huang et al., Nephrol Dial. Transplant, 24:743-754 (2009).

Annexin A1, also known as Lipocortin I, is a $Ca^{2+}$-dependent phospholipid-binding protein having a molecular weight of approximately 35,000 to 40,000. The amino acid sequence and gene sequence of mouse Annexin A1 can be found in GenBank (e.g., GenBank accession numbers NP_034860; 17 May 2009 and NM_010730; 17 May 2009, respectively) and the amino acid/gene sequences of human Annexin A1 can be found in GenBank (e.g., GenBank accession numbers AAH35993; 15 Jul. 2006 and BC035993; 15 Jul. 2009).

Rab23 is a small GTPase involved in the hedgehog signaling pathway. Mouse Rab23 is presented in GenBank with accession numbers NM_001153201 (amino acid sequence, 10 May 2009) and NM_008999 (gene sequence, 10 May 2009). Human Rab23 can be found in GenBank with accession numbers BAA87324 (amino acid sequence, 19 Feb. 2008) and AB034244.1 (gene sequence, 19 Feb. 2008).

To diagnose a renal disease by the method of this invention, a renal sample is obtained from a subject who is suspected of having the disease and the level of Annexin A1 or Rab23 in the sample is determined. An elevated level of either Annexin A1 or Rab23 in the renal sample relative to that of a healthy subject indicates that the subject is either suffering from the disease or at risk for developing the disease. The term "a renal sample" used herein refers to a biosample that is commonly used for diagnosing a kidney disease. Examples include, but are not limited to, a kidney tissue sample and a urine sample. The level of Annexin A1 or Rab23 can be determined by examining either its protein or mRNA level via conventional methods. For example, the protein level can be determined by, e.g., immunohistochemistry, westernblot, SDS-PAGE, or 2-dimensional electrophoresis and the mRNA level can be determined by, e.g., real-time RT-PCR.

When Rab23 is used as the marker, its level also can be determined by examining the protein or mRNA level of one or more other components of the hedgehog signaling pathway, e.g., Shh, Ihh, Dhh, PTCH1, PTCH2, SMO, Gli1, Gli2, and Gli3. Table 1 below lists the GenBank accession numbers of these components (mouse and human, referring to the most updated versions available as of Jun. 15, 2009).

TABLE 1

Human and Mouse Hedgehog Signaling Pathway Components

| Hedgehog Signaling Pathway Components | Mouse | Human |
|---|---|---|
| Shh | NM_009170 | NM_000193 |
| Ihh | NM_010544 | NM_002181 |
| PTCH1 | NM_008957 | NM_000264 |
| PTCH2 | NM_008958 | NM_003738 |
| SMO | NM_176996 | NM_005631 |
| Gli1 | NM_010296 | NM_001160045 |
| Gli2 | NM_001081125 | NM_005270 |
| Gli3 | NM_008130 | NM_000168 |

To assess the efficacy of a kidney disease treatment in a patient, renal samples are obtained from that patient before and after the treatment and the levels of either Annexin A1 or Rab23 in the samples are determined as described above. A decreased level of either Annexin A1 or Rab23 after the treatment is indicative of its effectiveness.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Correlation Between Annexin A1 and Renal Disease in Humans

Urine samples and kidney tissue samples were collected from 55 patients suffering from various kidney diseases and 10 healthy volunteers. All of the patients and healthy volunteers are Mongolian. The clinical data of the patients are shown in Table 2 below:

TABLE 2

Clinical Data of Kidney Disease Patients

| Patient | Age/Gender | Diagnosis | Clinical features Daily protein loss (mg/day) | SCr (mg/dl) | BUN (mg/dl) | CCR (ml/min) |
|---|---|---|---|---|---|---|
| 1 | 75/ | Crescentic GN | | 7.6 | 56 | |
| 2 | 47/ | Chronic GN | 1242 | 14.5 | 112 | |
| 3 | 55/ | Focal necrotizing glomerulonephritis with crescentic and global glomerulosclerosis | 2550 | 1.4 | 21 | |
| 4 | 29/ | End-stage renal disease | 1092 | 10.7 | 108 | |
| 5 | 31/ | End-stage renal disease | 1092 | 8.1 | 76 | 4.9 |
| 6 | 58/ | Interstitial nephritis with focal glomerular sclerosis | 1235 | 2.7 | 56 | 17.96 |
| 7 | 41/ | c/w IgAN with global sclerosis | | 1.4 | 16 | |
| 8 | 61/ | MGN with focal global sclerosis | 2862 | 0.4 | 18 | 120.13 |
| 9 | 38/ | c/w Beroga nephrosclerosis | 1670 | 7.4 | 103 | 15.79 |
| 10 | 35/ | Global sclerosis | 18644 | 0.8 | 21 | 133.93 |
| 11 | 23/ | MsPGN with glomerulosclerosis and interstitial nephritis | 2414 | 0.9 | 14 | |
| 12 | 68/ | Interstitial nephritis with focal glomerular sclerosis | | 4.1 | 70 | 15.65 |
| 13 | 54/ | Glomerulosclerosis | 3528 | 4.8 | 47 | 18.33 |
| 14 | 75/ | c/w FSGS in chroni GN stage | 95 | 3.2 | 45 | 29.11 |
| 15 | 77/ | FSGS | | 1.7 | 25 | |
| 16 | 21/ | FSGS | 225.5 | 0.9 | 10 | 89.85 |
| 17 | 52/ | FSGS | 4576 | 0.9 | 31 | 50.7 |
| 18 | 51/ | c/w Diabetic nephropathy | 23276 | 10 | 63 | |
| 19 | 42/ | c/w Diabetic nephropathy | | 10.4 | 101 | |
| 20 | 65/ | c/w Diabetic nephropathy | 6741 | 1.1 | 24 | 49.84 |
| 21 | 39/ | c/w Diabetic nephropathy | | 0.7 | 15 | |
| 22 | 69/ | c/w Diabetic nephropathy | 7079 | 0.5 | 18 | |
| 23 | 15/ | IgAN | | 0.6 | 16 | |
| 24 | 24/ | IgAN | | 1.2 | 11 | |
| 25 | 31/ | IgAN | | 0.8 | 17 | |
| 26 | 29/ | IgAN | | | 19 | |
| 27 | 28/ | Lupus nephritis 4c | 5670 | 0.6 | 11 | |
| 28 | 34/ | Lupus nephritis 4c | 3744 | 4.2 | 66 | |
| 29 | 34/ | Lupus nephritis 4c | 4587 | 11.2 | 126 | |
| 30 | 44/ | Lupus nephritis 4c | 1127 | 0.6 | 17 | |
| 31 | 27/ | Lupus nephritis 4c | 2430 | 1.6 | 36 | |
| 32 | 25/ | Lupus nephritis 4c | 1960 | 9 | 53 | |
| 33 | 87/ | MGN | | 3.8 | 44 | |
| 34 | 46/ | MGN | | 0.7 | 20 | |
| 35 | 40/ | MGN | | 0.7 | 7 | |
| 36 | 74/ | MGN | 9295 | 2.6 | 55 | 11.75 |

TABLE 2-continued

Clinical Data of Kidney Disease Patients

| Patient | Age/Gender | Diagnosis | Clinical features Daily protein loss (mg/day) | Renal function | | |
|---|---|---|---|---|---|---|
| | | | | SCr (mg/dl) | BUN (mg/dl) | CCR (ml/min) |
| 37 | 26/ | Chronic GN with interstitial nephritis | 1569 | 12.4 | 109 | 17.1 |
| 38 | 78/ | Focal segmental necrotizing GN with interstitial nephritis | 9000 | 2.4 | 75 | 20.87 |
| 39 | 60/ | Interstitial nephritis | 1726 | 3.1 | 56 | 24.52 |
| 40 | 59/ | Chronic GN with interstitial nephritis | 1200 | 7.6 | 85 | 4.09 |
| 41 | 53/ | Interstitial nephritis | | 1.1 | 17 | |
| 42 | 55/ | Chronic glomerulonephritis with interstitial nephritis | | 4.1 | 64 | |
| 43 | 70/ | Chronic GN with interstitial nephritis | | 3.7 | 69 | 18.66 |
| 44 | 19/ | Chronic interstitial nephritis | 3604 | 16.9 | 132 | 1.15 |
| 45 | 25/ | proliferation GN | 1309 | 1 | 10 | 33.35 |
| 46 | 47/ | Chronic GN | 1240 | 25.4 | 187 | 0.77 |
| 47 | 53/ | Chronic GN | | 3.6 | 39 | |
| 48 | 67/ | MPGN | | 1.6 | 33 | 30.31 |
| 49 | 28/ | Glomerular focal hyalinosis | 12925 | 1.1 | 11 | 150.51 |
| 50 | 27/ | c/w ATN | 1700 | 1.6 | 80 | 50.99 |
| 51 | 23/ | MCD | 15190 | 0.9 | 11 | |
| 52 | 29/ | MCD | | 0.9 | 13 | |
| 53 | 25/ | MCD | 1665 | 1 | 15 | 138.33 |
| 54 | 25/ | MCD | 2451 | 1 | 16 | 106 |
| 55 | 22/ | MCD | 90 | 0.7 | 8 | 73.2 |

The Annexin A1 levels in these samples were examined as follows.

First, an immunohistochemical staining (IHC) assay was performed to detect the protein levels of Annexin A1 in kidney tissue samples. Briefly, the kidney tissue samples were formalin-fixed and paraffin-embedded following routine procedures. After removal of paraffin, the samples were heated in a microwave for 10 mins (for antigen retrieval) and then cooled to 25° C. for 20 minutes. Afterwards, the samples were immersed in 5% bovine serum albumin to reduce staining background. The samples were then incubated with an anti-human Annexin A1 antibody (BD biosciences) at 4° C. overnight. After being washed several times to remove unbound antibodies, the samples were first incubated with a biotinylated anti-human IgG antibody and then with reactants for signal development. The staining patterns of the samples were observed using a microscope. Results obtained from this assay indicate that the protein levels of Annexin A1 are significantly higher in the kidney tissue samples obtained from the patients than in the kidney tissue samples obtained from the volunteers.

Next, an in-situ hybridization (ISH) assay was performed to examine the message RNA (mRNA) levels of Annexin A1 in tissue samples obtained from both the patients and the volunteers. The following primers were used to produce a DNA fragment encoding human Annexin A1: forward primer: 5'-TTGAGGAGGTTGTTTTAGCTCTG-3' (SEQ ID NO.: 1); reverse primer: 5'-AGTTCTTGATGCCAAAATCT-CAA-3' (SEQ ID NO.: 2). The PCR product was cloned into pGEM-T EASY vector (Promega, Wis., USA) and in vitro transcription was performed to produce a digoxigenin-labeled RNA probe, which is complementary to the mRNA of Annexin A1. This probe was used to hybridize with the tissue samples mentioned above. Briefly, the tissue samples were formalin-fixed and paraffin-embedded following routine procedures. After removal of paraffin, the samples were treated 20 μg/ml Proteinase K (Sigma, Mo., USA). They were then hybridized with the digoxigenin-labeled RNA probe mentioned above in a hybridization solution containing 2 mmol/L ethylenediaminetetraacetic acid (EDTA), 20 mmol/L Tris, pH7.5, 0.6 mol/L NaCl, 2×Denhardt's solution, 20% dextran sulfate, 0.1 mg/mL tRNA, and 0.2 mol/L DTT. The hybridization reaction was carried out at 42° C. for 16 hrs. After being washed, the samples were soaked in 1× blocking solution (Roche, Ind., USA) and incubated with an anti-digoxigenin antibody conjugated with alkaline phosphatase for 1 hour. Substrate NBT/BCIP was then added for color development. The samples were further incubated with methyl green (for nuclear staining) and then observed using a microscope. Results thus obtained show that the levels of Annexin A1 mRNA are high in kidney tissues obtained from the patients, particularly in glomerular endothelial cells, mesangial cells, and damaged kidney areas (e.g., glomerular fibrosis areaes, areas where inflammatory cells infiltrated). Differently, the Annexin A1 mRNA levels in healthy volunteers are much lower. These results are consistent with those obtained from the IHC assay described above.

Finally, the protein levels of Annexin A1 in urine samples collected from the 55 patients and 10 healthy volunteers mentioned above were examined by westernblot as follows. The urine samples were centrifuged at 1000 g for 10 mins. If necessary, the supernants were mixed with 1% antiproteinase (Roche, Ind., USA) and stored at −70° C. for further analysis. The supernatants were mixed with 1× sample buffer (10% SDS, 2 ml glycerol, 100 mM DTT, 145 mg Tris, and 0.05% bromophenol blue) and incubated on ice for 15-20 minutes. The proteins contained in the mixtures were separated by SDS-Polyacrylamide Gel Eletrophoresis (SDS-PAGE; 10%)

and transferred to a nitrocellulose membrane. The membrane was treated with a blocking buffer (5% non-fat milk) for 2 hrs, incubated with an anti-human AnxA1 antibody (BD biosciences) at 4° C. overnight, and then incubated with a horseradish peroxidase-conjugated anti-human IgG antibody at room temperature for 1 hr. The membrane was washed several times and incubated with a chemiluminescent reagent (PerkinElmer Life Sciences, Boston, Mass.) for signal development. The results thus obtained were normalized against the creatine levels in the same urine samples. Annexin A1 protein was detected in urine samples of patients with various renal disorders. As shown in FIG. 1, the amounts of Annexin A1 protein in the patient urine samples are significantly higher than those in the healthy volunteers.

Taken together, the results discussed above indicate that Annexin A1 is a biomarker associated with kidney disease.

Example 2

Correlation Between Rab23 and Focal Segmental Glomerulosclerosis in Mice 8-week-old BALB/c mice were injected with adriamycin (0.1 mg/per 10 g body weight) intravenously to induce Focal Segmental Glomerulosclerosis (FSGS). Blood, urine, and kidney tissue samples were collected at days 0, 7, 15, and 20 after injection. More specifically, the blood samples were collected from the retro-orbital venous plexus and the urine samples were collected by gentle abdominal massage. The samples were centrifuged to remove insoluble substances and then stored in liquid nitrogen. When urine proteins are to be measured, the corresponding samples were collected on parafilms. The modified Bradford protein assay was performed to examine urine protein concentration, the picric acid colorimetric kit (Sigma 555-1) was used for detecting creatinine, and an urease assay kit provided by Sigma (640-5) was used for determining the level of blood urea nitrogen (BUN).

Figure 2:
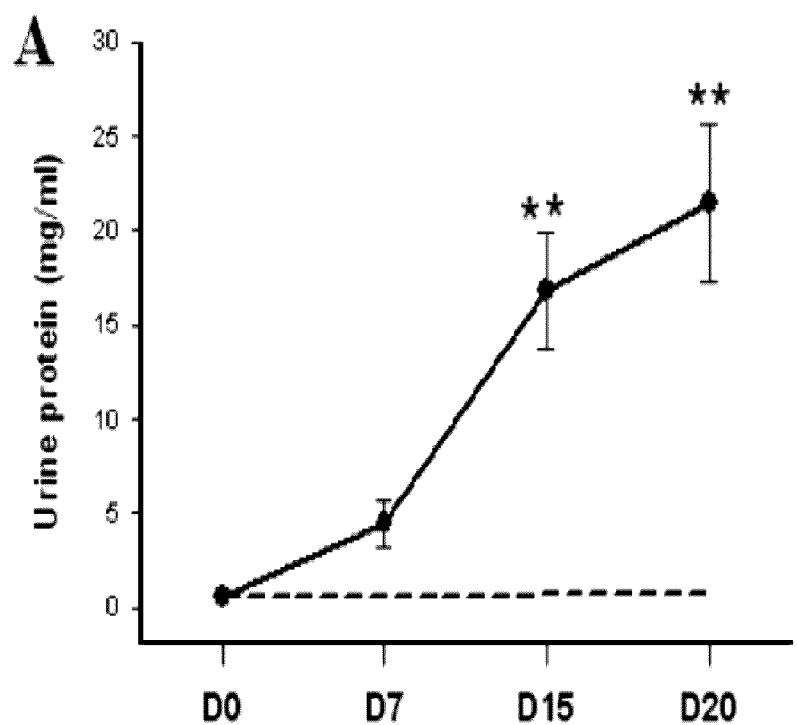
FIG. 2 is a diagram showing that focal segmental glomerulosclerosis (FSGS) progresses over time in a mouse model. Panel A: a chart showing increase of urine protein levels over time. Panel B: a chart showing increase of serum creatinine levels over time. Panel C: a chart showing increase of blood urea nitrogen levels over time.
Figure 2:
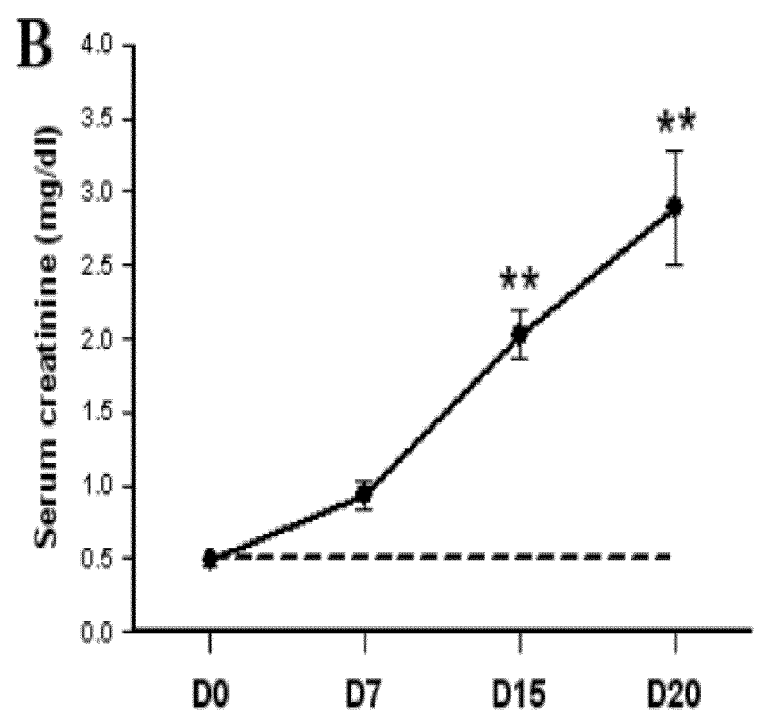
Figure 2:
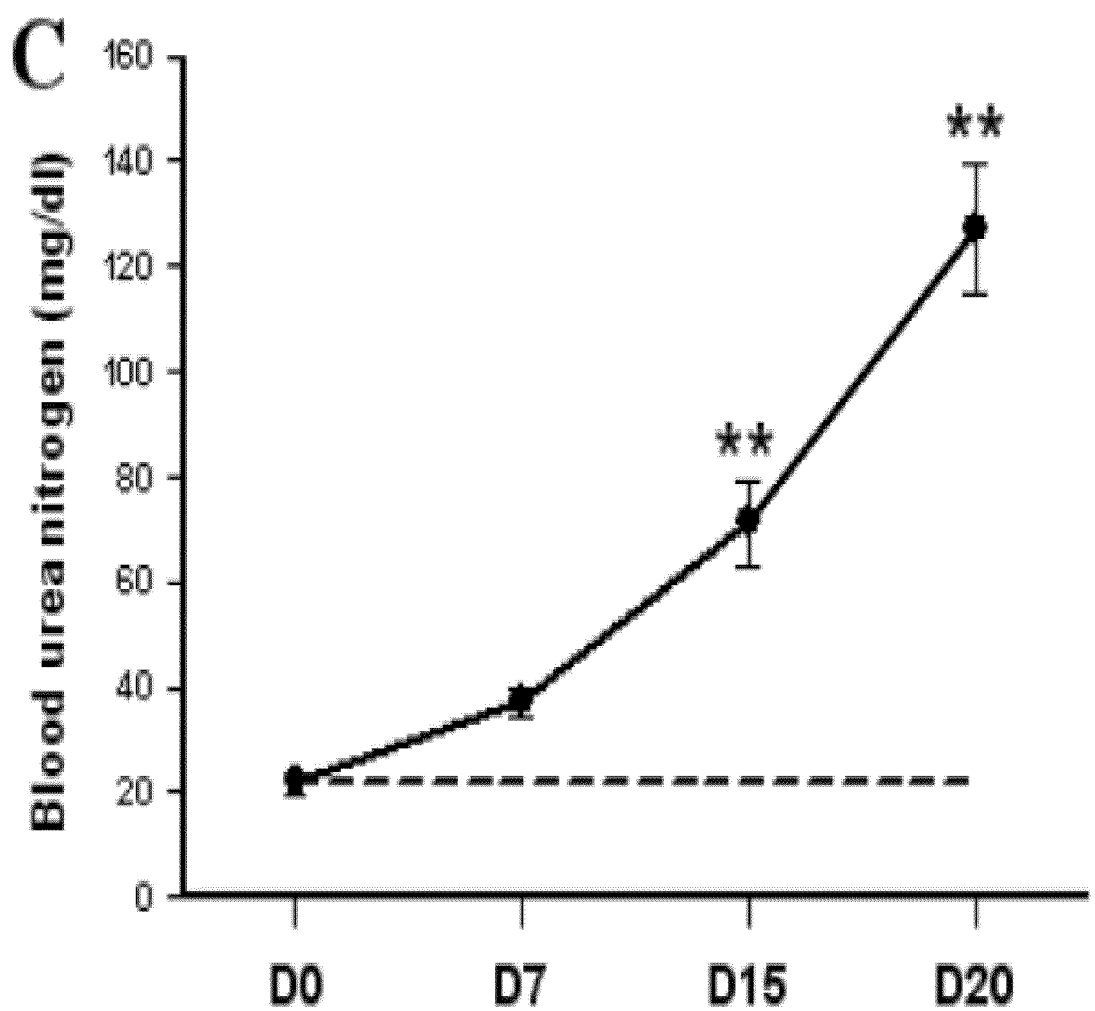

Adriamycin treatment resulted in severe propeinuria and reduced renal clearance function. Compared with the control mice, the mice treated with adriamycin showed substantially increased urine protein levels on day 15 (i.e., 0.59±0.082 versus 16.84±3.13 mg/ml, F=13.81, P<0.01). See FIG. 2A. The levels of serum creatinine and BUN, two common parameters for evaluating renal functions, are also higher in the adriamycin-treated mice than in the control mice. More specifically, on day 15, the serum creatinine level in treated mice is 2.02±0.17 mg/dl, much higher than that in the control mice, i.e., 0.48±0.03 mg/dl (F=25.17, p<0.01) and the BUN level in treated mice is 71.42±8.09 mg/dl, also much higher than that in the control mice, i.e., 21.85±1.99 mg/dl (F=38.79, p<0.01). See FIGS. 2B and 2C.

The protein levels of Rab23 in the urine samples were analyzed by a 2-dimentional isoelectro focusing (IEF)/SDS-PAGE assay. The urine samples obtained from both FSGS mice and control mice were subjected to ultrafiltration, desalination and concentration. They were then loaded onto an Immobiline DryStrip gel (3-10, GE Healthcare, N.J., USA) with immobilized pH gradient (IPG) for simultaneous rehydration. After being separated by IEF, the proteins were subjected to SDS-PAGE analysis. The protein migrated to the position corresponding to Rab23 was eluted and digested with trypsin. The resultant peptides were analyzed by mass spectrometry, using Bruker Biflex IV MADLI-TOF MS (Bruker Daltonics, Bremen, Germany). Peptide mass fingerprinting (PMF) was obtained based on the signals generated by 500 laser shots. The data thus obtained were analyzed using Flexanalysis™ and BioTools™ software (Bruker Daltonics, Bremen, Germany). By searching against the UniProt database (http://www.pir.uniprot.org) with the MS-Fit database searching engine, the amino acid sequences of the peptides were obtained, which match 10 Rab23 fragments. In this assay, Rab23 was detected in the urine samples obtained from the FSGS mice but not the control mice, indicating that the expression of this protein is only detectable in mice having kidney disease.

Figure 3:
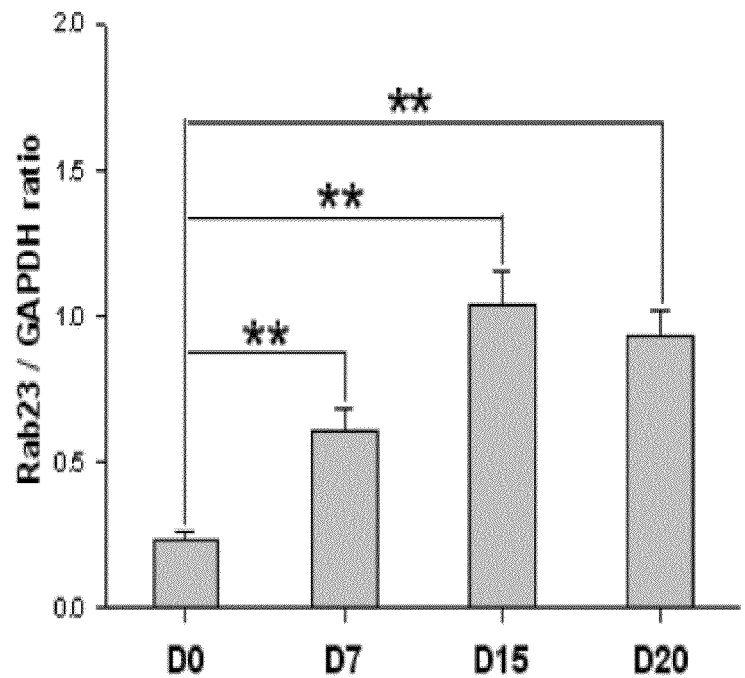
FIG. 3 is a diagram showing the correlation between the levels of Rab23 in kidney tissues and the progress of FSGS in a mouse model. Panel A: a chart showing that the protein levels of Rab23 in kidney tissues increase over time. Panel B: a chart showing that protein levels of Rab23 in kidney tissues increase over time.
Figure 3:
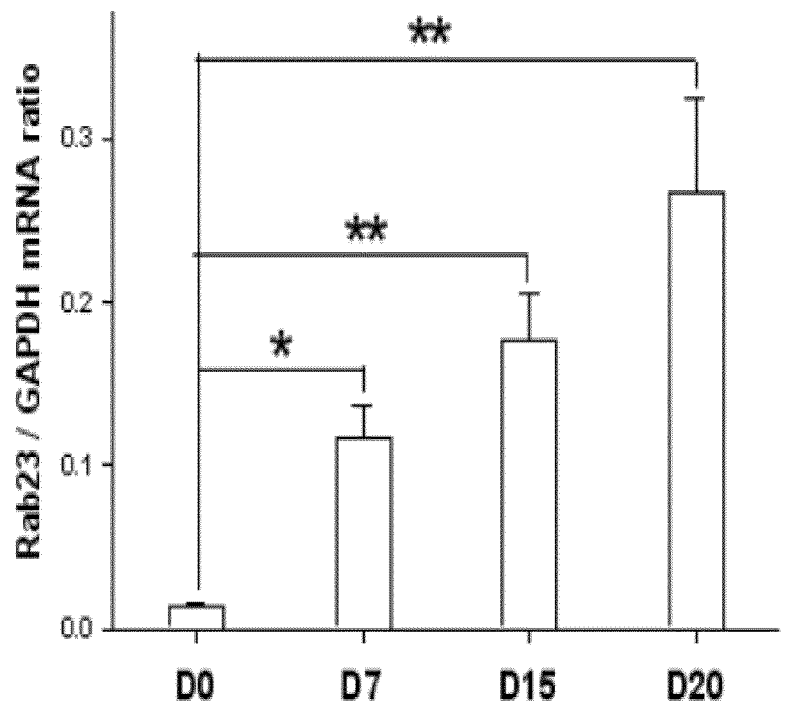

The protein levels of Rab23 were also examined by westernblot. 15 µl of each urine sample, 15 µl of each blood sample, 50 µg kidney proteins extracted from each tissue sample, and 50 µg proteins extracted from cultured rat mesangial cells were separated by SDS-PAGE (10%). The proteins were then transferred to a Hybond PVDF membrane (GE Healthcare, N.J., USA). The membrane was blocked in 20 ml blocking buffer (Tris-buffered saline, pH 8.0, containing 0.05% Tween-20 (TBST) and 5% skimmed milk) at room temperature for 1 hr, incubated with a rabbit anti-Rab23 antibody (1:1000) at room temperature for 1 hr, washed three times with TBST, and incubated with a goat anti-rabbit IgG antibody at room temperature for 1 hr. An ECL kit was used for color development. The intensity of the color was quantified with a densitometer. The data thus obtained were normalized against the levels of GAPDH in the same samples. Rab23 protein was detected in the urine samples of FSGS mice collected on days 7, 15, and 20. The levels of Rab23 protein were significantly increased on days 15 and 20 as compared to that on day 7. See FIG. 3A.

Next, kidney tissue samples obtained from both FSGS mice and control mice were subjected to immunostaining. The tissue samples, obtained on days 0, 7, 15, and 20 after injection of adriamycin, were OCT-embedded and cut into sections having a thickness of 5-µm. The sections were immersed in acetone for 5 mins. After being air dried, the sections were first incubated in a Tris buffered saline (TBS, pH=7.4) containing 0.05% Tween 20 (TBST) and 2% bovine serum albumin at room temperature for 30 mins, then with a rabbit anti-mouse Rab23 (1:200 dilution) antibody alone, or with both the anti-Rab23 antibody (1:150) and a goat anti-nephrin (1:20) (Santa Cruz) at 4° C. overnight. Nephrin is a marker of mesangial cells. After being washed with TBST, the sections were incubated with a horseradish peroxidease (HRP)-conjugated goat anti-rabbit IgG antibody (1:200) (Jackson ImmunoResearch, West Grove, Pa.) or a combination of fluorescein isothiocyanate (FITC)-conjugated donkey anti-rabbit IgG antibody (1:500) (Jackson ImmunoResearch, West Grove, Pa.) and Alexa Fluor 594-conjugated donkey anti-goat IgG antibody (1:500)(Invitrogen, Calif., USA) at room temperature for 1 hr. Substrate 3,3'-diaminobenzidine (DAKO, Carpinteria, Calif.) was used for signal development. The sections were also counterstained with hematoxylin. The intensity of the signals released from each section was semi-quantified under an optical microscope. Briefly, 50 glomeruli were examined on each slide and a score ranging from 0 to 3 was assigned to glomeruli, podocytes and mesangial cells based on the signal intensities thereof. The score of the total intensity was calculated as follows:

Total intensity score=[(negative intensity) %×0]+[(very weak intensity) %×0.5]+[(intensity score being 1)%×1]+[(intensity score being 2)%× 2]+[(intensity score being 3)%×3)].

As compared with the control mice, the FSGS mice showed a much higher expression levels of Rab23, particularly in mesangial cells. The intensity scores of the mesangial cells in the FSGS mice at days 7, 15, and 20 are 145.33±17.83, 189.33±21.63, and 219.17±24.78, respectively, which are much higher than the mean intensity score of the control mice, i.e., 67.33±4.72. The protein levels of Rab23 in the kidney tissue samples of the FSGS mice also increased along with disease progress. At day 7, the intensity score representing the Rab23 protein level is 0.61±0.078 while at days 15 and 20, this score increased to 1.02±0.11 and 0.93±0.090, respectively (p<0.01). These results indicate that the expression level of Rab23 correlates to disease severity.

The levels of Rab23 in the kidney tissues of the FSGS mice and control mice were further analyzed by examining its mRNA levels. Total RNAs were extracted from kidney tissues using the Trizol reagent (Life Technologies, Rockville, Md.). 3 μg of the total RNAs were mixed with 200 ng random primers, 0.5 mM dNTPs, 1× first stand buffer, 5 mM DTT, 10 units of reverse transcriptase (Invitrogen, Calif., USA) in a total volume of 20 μl for EDNA synthesis via reverse transcription (RT). The cDNA products were subjected to polymerase chain reaction as follows. 10 μl of the RT reaction mixture was mixed with 0.1 μM of the primers 5'-GAAG-GAGGACC TCAACGTGAGTGA-3' (forward primer SEQ ID NO.: 3) and 5'-CCAAGTGACTTCTGACCGATGCA-3' (reverse primer, SEQ ID NO.: 4), 1×PCR buffer, 50 μM dNTPs, 1 unit of KlenTaq DNA polymerase, and 12.5 μl Bio-Rad iQ SYBR Green supermix in a total volume of 25 μl, using the Cycler real-time PCR instrument provided by Bio-Rad. The PCR reaction was carried out under the following conditions:

initial denaturation and enzyme activation: 95° C. for 15 mins;

amplification: 94° C. for 15 s, 55° C. for 35 s, and 72° C. for 60 s, 50 cycles; and final elongation: 72° C. for 10 mins.

The amounts of the PCR products were quantified, normalized against the amounts of GAPDH mRNA in the same samples using a comparative threshold cycle ($2^{-[delta]Ct}$) method. The data thus obtained, expressed as means± standard errors of the means (SEM), were analyzed by one-way analysis of variance (ANOVA) using the SPSS software. The Newman-Keuls test was performed to determine the p-values of the ANOVA results. $P<0.05$ indicates that the results are statistically significant.

In kidney tissue samples obtained from the FSGS mice at different time points, the Rab23 mRNA levels at days 7, 15, and 20 were 0.12±0.019, 0.18±0.028, and 0.27±0.059, respectively. See FIG. 3B. These levels are much higher than the Rab23 mRNA level in the control mice, i.e., 0.013±0.0025 (p<0.01). This result indicates that the Rab23 levels correlate with FSGS severity.

The mRNA level of Rab23 was also examined in mouse mesangial cell line CRL-1927, following the same procedures described above. The results indicate that Rab23 is expressed at high levels in mesangial cells.

Example 3

Correlation Between Levels of Rab23 and Kidney Disease in Humans

The Rab23 levels in the kidney tissue samples as described above, obtained from the 55 human patients and 10 healthy volunteers, were first examined by immunostaining. The tissues were cut into sections. The sections were first incubated in TBS (Tris buffered saline, pH=7.4) containing 0.05% Tween 20 (TBST) and 2% bovine serum albumin at room temperature for 30 mins, and then incubated with a rabbit anti-human Rab23 antibody (1:200 dilution) at 4° C. overnight. After being washed with TBST, the sections were further incubated with a horseradish peroxidease (HRP)-conjugated goat anti-rabbit IgG antibody (1:200) (Jackson ImmunoResearch, West Grove, Pa.) at room temperature for 1 hr. Substrate 3,3'-diaminobenzidine (DAKO, Carpinteria, Calif.) was then added for signal development. The sections were also counterstained with hematoxylin. The intensities of the signals were semi-quantitated using an optical microscope. Rab23 was found to be expressed at high levels in podocytes and wall cells of glomeruli in the kidney tissue samples obtained from the patients, while only very lower levels of Rab23 were detected in the kidney tissue samples of the healthy volunteers.

The Rab23 levels in the urine samples obtained from both the human patients and volunteers were further determined by western blot following the procedures described in Example 2 above. The protein levels as shown in the westernblot were quantified and normalized against the creatinine concentrations in the same urine samples. Results thus obtained indicate that the levels of Rab23 in the patient urine samples are higher than those in the urine samples of the healthy volunteers.

Finally, the Rab23 levels in the kidney tissue samples were examined by real-time RT-PCR, following the procedures described in Example 2 above. The results are consistent with those described above.

Taken together, this study demonstrates that Rab23 is a biomarker of kidney disease.

Example 4

Figure 4:
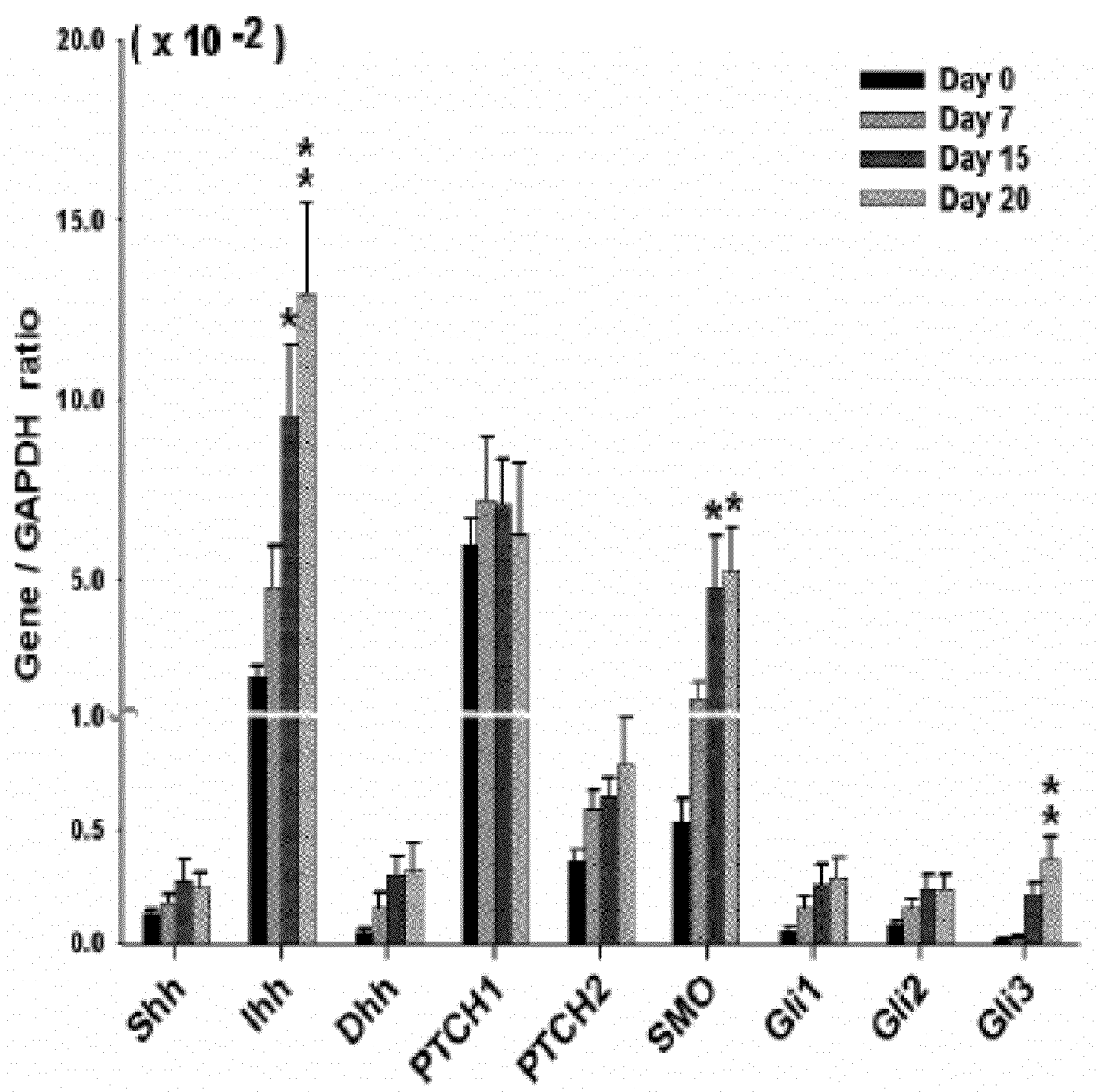
FIG. 4 is a chart showing that the expression levels of hedgehog signaling pathway genes increase in kidney tissues of FSGS mice over time.

Determining Levels Hedgehog Signaling Pathway Components in FSGS Mouse Kidney Tissues The expression levels of hedgehog signaling pathway genes, i.e., Shh, Ihh, Dhh, PTCH1, PTCH2, SMO, Gli1, Gli 2, and Gli3, were determined by real-time RT-PCR following the method described in Example 2 above. As shown in FIG. 4, these genes were expressed in kidney tissues of the FSGS mice and their expression levels correlate with disease severity. This result indicates that the level of any of these hedgehog signaling pathway components, or their combination, can be used for kidney disease diagnosis and prognosis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for diagnosing a renal disorder in the kidney of a subject, comprising:
   providing a renal sample obtained from a subject suspected of having a glomerulonephritis or a renal fibrosis;
   detecting the level of a biomarker in the renal sample; and
   determining whether the subject has the glomerulonephritis or the renal fibrosis based on the level of the biomarker thus detected;
   wherein the biomarker is Annexin A1 and an elevated level of the biomarker in the subject relative to that in a healthy subject indicates that the subject has the Annexin A1 which appears in the kidney tissue sample while the kidney has the glomerulonephritis or the renal fibrosis.

2. The method of claim 1, wherein the detecting step is performed by examining the protein level of Annexin A1.

3. The method of claim 1, wherein the detecting step is performed by examining the message RNA level of Annexin A1.

4. The method of claim 1, wherein the biomarker is Rab23.

5. The method of claim 4, wherein the detecting step is performed by examining the protein level of Rab23.

6. The method of claim 4, wherein the detecting step is performed by examining the message RNA level of Rab23.

7. The method of claim 4, wherein the detecting step is performed by examining the amount of Shh, Ihh, Dhh, PTCH1, PTCH2, SMO, Gli1, Gli2, Gli3, or a combination thereof, and determining the level of Rab23 based on the amount thus obtained.

8. The method of claim 4, wherein the renal disorder is selected from the group consisting of kidney sclerosis, kidney fibrosis, glomerular injury, kidney failure, glomerulosclerosis, and glomerulonephritis.

* * * * *